United States Patent [19]
Ha et al.

[11] Patent Number: 6,159,195
[45] Date of Patent: Dec. 12, 2000

[54] EXCHANGE CATHETER AND METHOD OF USE

[75] Inventors: Hung V. Ha, San Jose; Celso J. Bagaoisan, Union City, both of Calif.

[73] Assignee: PercuSurge, Inc., Sunnyvale, Calif.

[21] Appl. No.: 09/026,464

[22] Filed: Feb. 19, 1998

[51] Int. Cl.⁷ .................................................. A61M 31/00
[52] U.S. Cl. ........................ 604/500; 604/523; 604/103.04
[58] Field of Search ...................... 604/48, 500, 507–510, 604/96, 523, 103.04; 606/191, 194

[56] References Cited

U.S. PATENT DOCUMENTS

| | | |
|---|---|---|
| 4,306,562 | 12/1981 | Osborne . |
| 4,748,982 | 6/1988 | Horzewski et al. . |
| 4,820,349 | 4/1989 | Saab . |
| 4,932,413 | 6/1990 | Shockey et al. . |
| 4,944,740 | 7/1990 | Buchbinder et al. . |
| 4,947,864 | 8/1990 | Shockey et al. . |
| 4,976,689 | 12/1990 | Buchbinder et al. . |
| 4,988,356 | 1/1991 | Crittenden et al. ...................... 606/192 |
| 5,234,407 | 8/1993 | Teirstein et al. . |
| 5,255,690 | 10/1993 | Keith et al. ............................... 128/772 |
| 5,263,932 | 11/1993 | Jang .......................................... 604/96 |
| 5,267,958 | 12/1993 | Buchbinder et al. ...................... 604/96 |
| 5,318,527 | 6/1994 | Hyde et al. . |
| 5,334,147 | 8/1994 | Johnson .................................... 604/96 |
| 5,336,184 | 8/1994 | Teirstein .................................. 604/102 |
| 5,342,297 | 8/1994 | Jang .......................................... 604/53 |
| 5,364,376 | 11/1994 | Horzewski et al. . |
| 5,387,226 | 2/1995 | Miraki ..................................... 606/194 |
| 5,395,335 | 3/1995 | Jang . |
| 5,425,709 | 6/1995 | Gambale . |
| 5,454,785 | 10/1995 | Smith ......................................... 604/49 |
| 5,468,225 | 11/1995 | Teirstein .................................. 604/102 |
| 5,549,551 | 8/1996 | Peacock, III et al. .................... 604/96 |
| 5,554,118 | 9/1996 | Jang .......................................... 604/96 |
| 5,571,086 | 11/1996 | Kaplan et al. ............................. 604/96 |
| 5,571,094 | 11/1996 | Sirhan ..................................... 604/284 |
| 5,630,427 | 5/1997 | Hastings .................................. 128/772 |
| 5,634,901 | 6/1997 | Alba et al. ................................ 604/96 |
| 5,645,533 | 7/1997 | Blaeser et al. . |
| 5,658,262 | 8/1997 | Castaneda et al. . |
| 5,667,521 | 9/1997 | Keown . |
| 5,690,120 | 11/1997 | Jacobsen et al. . |
| 5,690,613 | 11/1997 | Verbeek . |
| 5,728,067 | 3/1998 | Enger ...................................... 604/102 |
| 5,779,673 | 7/1998 | Roth et al. .............................. 604/101 |
| 5,833,644 | 11/1998 | Zadno-Azizi et al. .................... 604/52 |
| 5,849,016 | 12/1998 | Suhr ........................................ 606/108 |
| 5,873,880 | 2/1999 | Williams et al. ........................ 606/108 |
| 5,947,925 | 9/1999 | Ashiya et al. ............................ 604/96 |
| 5,980,486 | 11/1999 | Enger ...................................... 604/102 |
| 6,022,336 | 2/2000 | Zadno-Azizi et al. .................... 604/96 |

*Primary Examiner*—Corrine McDermott
*Assistant Examiner*—Cris L. Rodriguez
*Attorney, Agent, or Firm*—Knobbe, Martens, Olson & Bear LLP

[57] ABSTRACT

Exchange catheters which allow for the removal of a standard guidewire and replacement with a guidewire or catheter bearing an occlusive device during percutaneous transluminal angioplasty or related procedures. The elongate catheters have at least one lumen, and are preferably provided with a slit approximately 3–20 mm in length at the distal end of the lumen to allow the catheter to expand to accommodate the passage of the occlusive device while still maintaining a low profile. The catheters can also be used to provide aspiration and/or delivery of fluid.

22 Claims, 8 Drawing Sheets

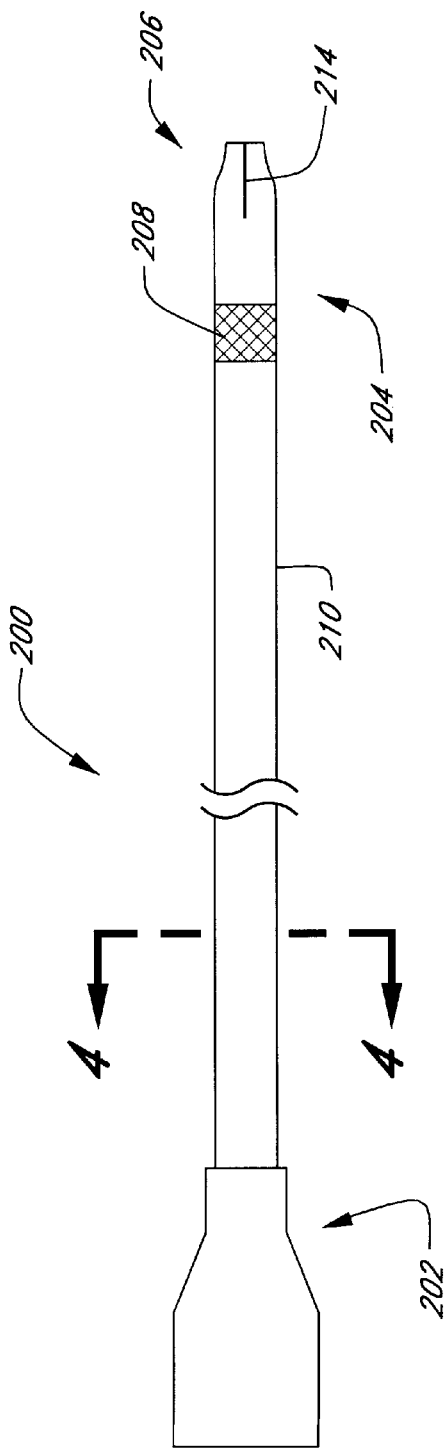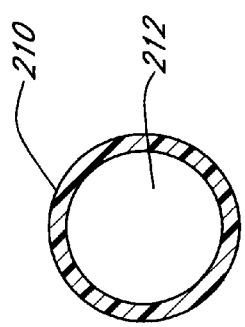
FIG. 3
FIG. 4

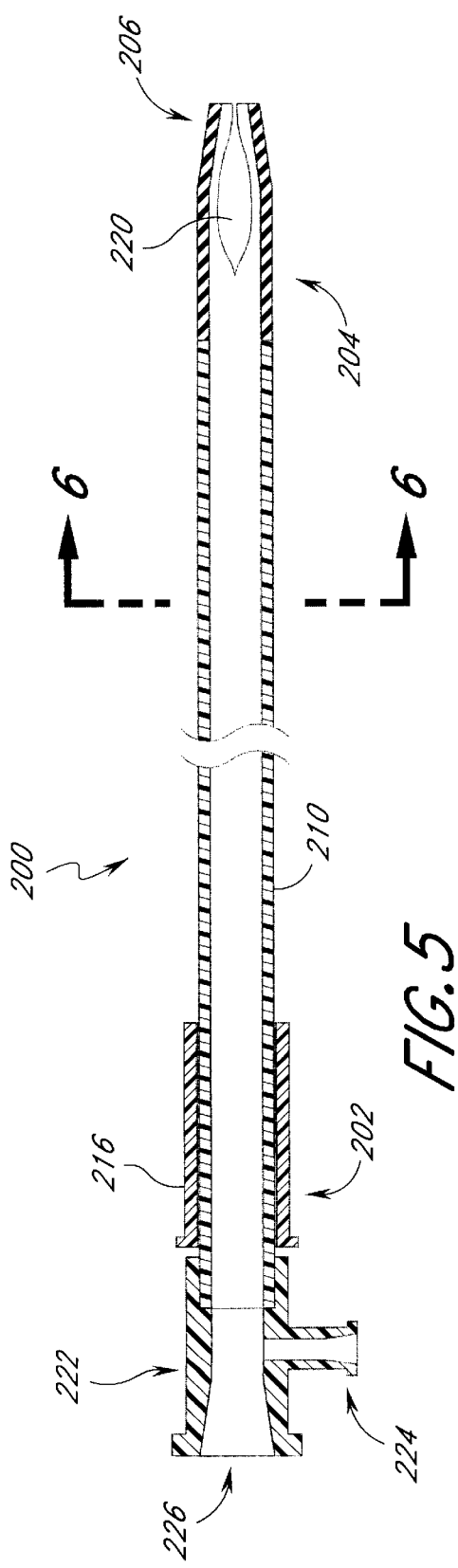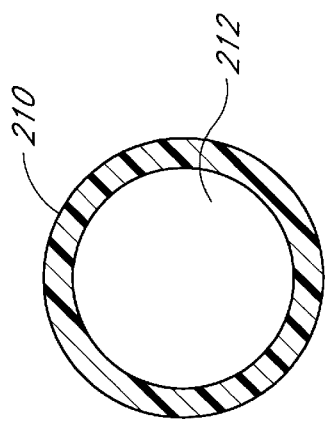

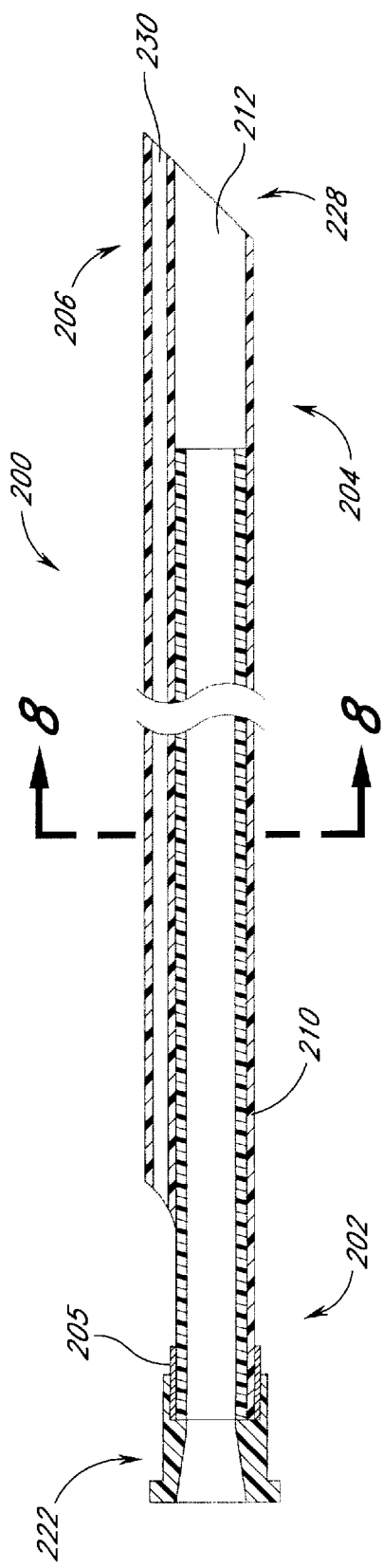
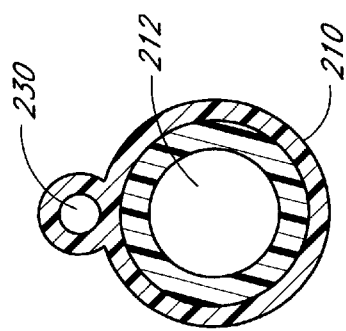
FIG. 7
FIG. 8

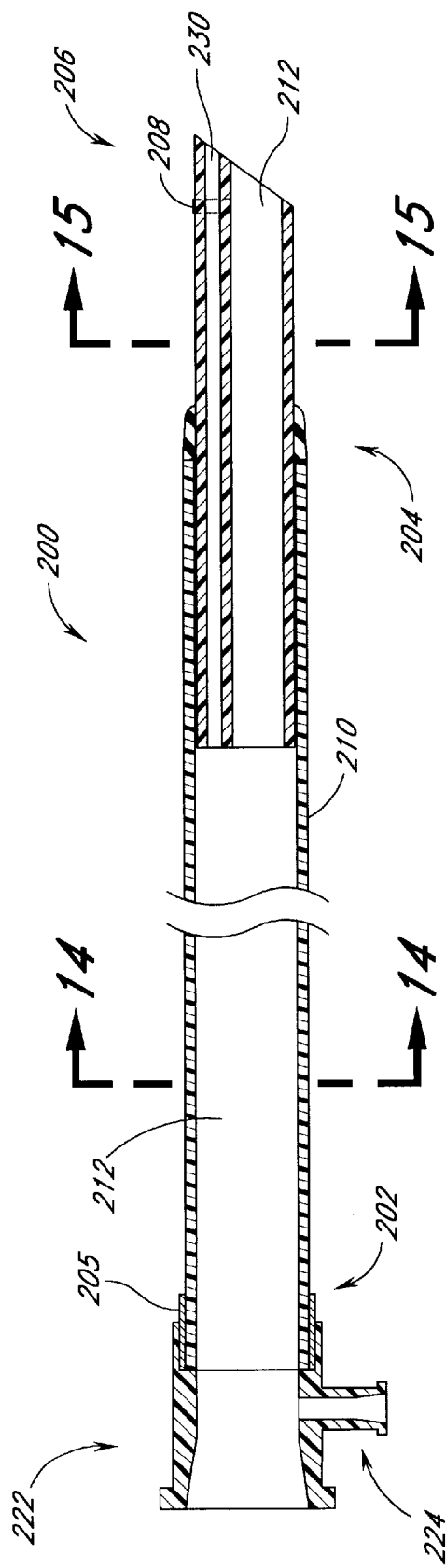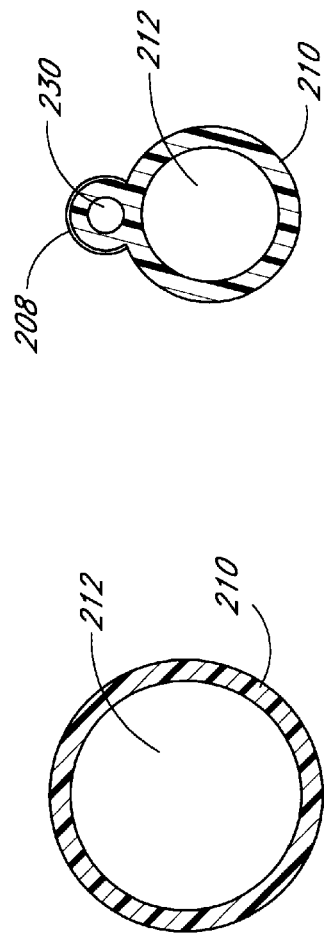

EXCHANGE CATHETER AND METHOD OF USE

BACKGROUND OF THE INVENTION

The present invention relates to medical catheters, and more particularly, to exchange catheters and methods of using such catheters.

Catheters are long, tube-like devices inserted into the body for various diagnostic and therapeutic purposes. Guide wires are often used to lead or guide the catheters to the desired location in the patient's body. For example, in percutaneous transluminal coronary angioplasty (PTCA), a guidewire is first inserted into the patient's femoral artery and is advanced to the site of a stenosis or occlusion. Fluoroscopy is used to view the arterial system in order to navigate the wire through the vasculature. A guide catheter is then typically inserted along the guidewire to a point just proximal to the occlusion.

Often, it is desirable to remove the first guidewire, and insert a second guidewire. The first guidewire may be exchanged for a second guidewire that is different in size or stiffness, or of a different shape, for example. The guidewires are exchanged while the guide catheter remains in place, and the wires are withdrawn and inserted through the catheter. The guide catheter may therefore also be known as an exchange catheter, or introducer.

In PTCA, an angioplasty catheter having an inflatable balloon at its distal end is inserted through the guide catheter and over the guidewire, until the angioplasty balloon is in place at the site of the occlusion. The balloon is then inflated to reduce the size of the occlusion and restore blood flow through the vessel.

It is preferable that the guide catheter or exchange catheter has as small a profile, i.e., transverse dimension, or outer diameter, as possible, especially at its distal tip. This is to reduce the risk of hematoma at the site of insertion in the femoral artery or other vessel, and to reduce the risk of injury to the vessels during advancement and removal of the catheter.

There is therefore a need for an exchange catheter which will allow for the exchange of guidewires and facilitate the insertion of occlusive devices, while also having a low profile to prevent damage to the patient's blood vessels.

SUMMARY OF THE INVENTION

The exchange catheters of the present invention allow for the removal of a standard guidewire and replacement with a guidewire or catheter bearing an occlusive device, such as a balloon, filter or coil, during percutaneous transluminal angioplasty or related procedures. The elongate catheters have at least one lumen, and are preferably provided with a slit approximately 3–20 mm in length at the distal end of the lumen to allow the catheter to expand to accommodate the passage of the occlusive device while still maintaining a low profile, thus reducing the risk of injury to the patient. The catheters can also be used to provide aspiration and/or delivery of fluid if desired.

The elongate catheters have at least one lumen extending from the proximal end of the catheter to the distal end. The proximal end of the catheter is preferably less flexible than the distal end, which provides the proximal end with sufficient structural integrity during advancement of the catheter, while the more flexible distal region is more readily advanced through the blood vessels. The distal end of the catheter is preferably tapered to a very small profile, which reduces the risk of injury to the patient while the catheter is manoeuvered inside the blood vessels.

The distal end of the catheter is preferably provided with at least one slit. The slit allows an occlusive device to pass through the distal end of the catheter, while still allowing the catheter to maintain a low profile during advancement of the catheter through the blood vessels.

The catheter of the present invention is preferably formed of a polymer, and can include a reinforcement, such as a braid or coil, along its length. The catheters can include such additional features as a radiopaque marker on the distal end to allow the user to view the distal end of the catheter within the patient's body during insertion using fluoroscopy. A support sheath can be mounted on the proximal end to provide added structural integrity. Various hubs and adaptors can be provided on the proximal end of the catheter to facilitate access to the lumen of the catheter, and to provide a connection to sources of aspiration pressure and/or irrigation fluid. An outer sleeve, preferably made of a polymer such as polyimide, may be used to surround the length of the catheter shaft and provide additional structural integrity.

In one embodiment, the distal end of the exchange catheter has an opening adapted to provide aspiration. The opening is also sized to allow for the passage of the occlusive device. This again allows the catheter to accommodate passage of an occlusive device, while still allowing the catheter to maintain a low profile during advancement of the catheter through the blood vessels.

In another embodiment, the catheter has both a first lumen and a second lumen adjacent one another. The first lumen is sized so as to receive the guidewire bearing an occlusive device therethrough, and the second lumen is sized to receive a standard guidewire. The guidewire lumen may extend the entire length of the catheter shaft, end just distal to the proximal end of the catheter, or extend from the distal end of the catheter in a proximal direction for a length that is approximately one-fourth the length of the catheter shaft.

The exchange catheter of the present invention is useful in angioplasty and similar procedures during which catheter exchange may occur. For example, in most angioplasty procedures, a guidewire is first introduced into the vasculature of a patient until the distal end of the guidewire is near the occlusion or stenosis. The exchange catheter is then delivered over the guidewire to a site either proximal to or distal to the occlusion or stenosis. The guidewire is then removed from the patient, and an occlusion catheter having an occlusive device mounted on its distal end is delivered through the lumen of the exchange catheter and positioned either just proximal to or just distal to the occlusion or stenosis. Because the distal end of the exchange catheter is provided with a slit or slits, the distal end can expand to allow the occlusive device to pass through while still maintaining a low profile during insertion. The exchange catheter may then be removed from the patient. A therapy catheter is then delivered to the site of the occlusion or stenosis, and therapy is performed to remove or reduce the occlusion or stenosis.

The occlusive device is preferably activated prior to performing therapy to remove or reduce the occlusion or stenosis, to provide a working area and to prevent particles and debris produced during therapy from migrating downstream. Aspiration is preferably performed following therapy, to remove any particles and debris. The aspiration pressure can be provided through the exchange catheter, is desired. If the delivery of irrigation fluid or contrast medium if desired, these too may be delivered through the exchange catheter.

The present invention allows for the rapid and easy exchange of guidewires and catheters during angioplasty and similar procedures. The exchange catheter and methods of use allow for the removal of a standard guidewire and replacement with a guidewire or catheter bearing an occlusive device, while still maintaining a low profile at the distal tip to avoid injury to the patient. The exchange catheter simplifies the angioplasty procedure, and decreases the time it takes to perform the procedure, thus presenting significant advantages over known technology.

BRIEF DESCRIPTION OF THE DRAWINGS

FIG. 3 is a side view of an exchange catheter of the present invention.

FIG. 4 is a cross-sectional view of the exchange catheter of FIG. 3 taken along line 4—4 of FIG. 3.

FIG. 5 is a cross-sectional view of another embodiment of the exchange catheter having a distal tip adapted to provide aspiration.

FIG. 6 is a cross-sectional view of the exchange catheter of FIG. 5, taken along line 6—6 of FIG. 5.

FIG. 7 is a cross-sectional view of a dual lumen exchange catheter.

FIG. 8 is a cross-sectional view of the catheter of FIG. 7, taken along line 8—8 of FIG. 7.

FIG. 13 is a cross-sectional view of an exchange catheter having a dual lumen at its distal end and a single lumen and its proximal end.

FIG. 14 is a cross-sectional view of the catheter of FIG. 13 taken along line 14—14 of FIG. 13.

FIG. 15 is a cross-sectional view of the catheter of FIG. 13 taken along line 15—15 of FIG. 13.

DETAILED DESCRIPTION OF THE PREFERRED EMBODIMENT

Figure 1:
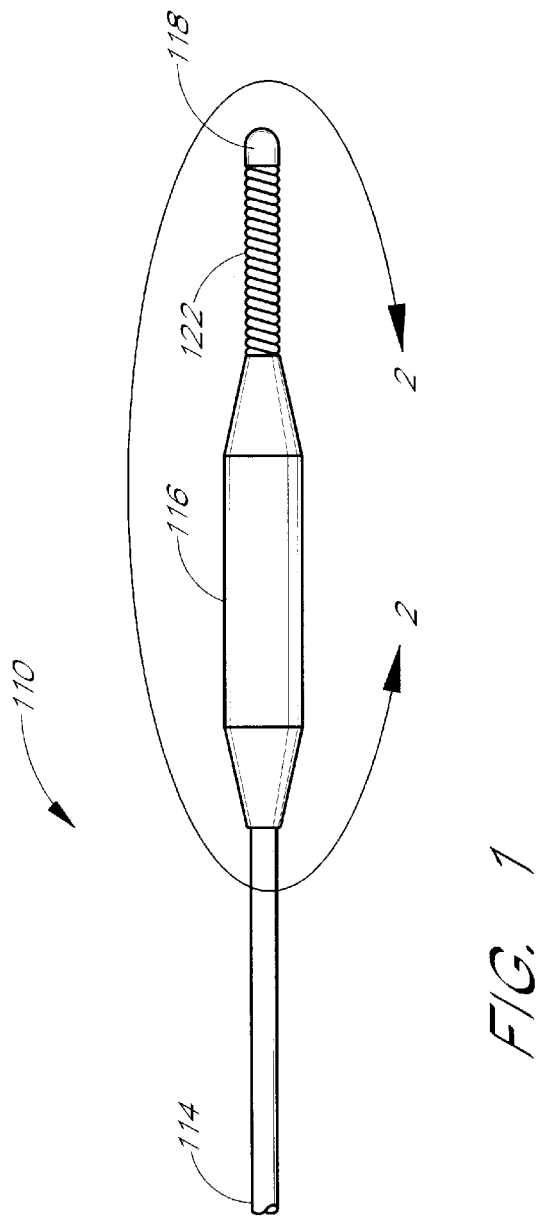
FIG. 1 is a schematic view of an occlusion catheter for use with the present invention.

The catheters of the present invention allow for the rapid and easy exchange of guidewires during angioplasty and similar procedures. In particular, the exchange catheters allow for the removal of a standard guidewire and replacement with a guidewire or catheter bearing an occlusive device. The catheters can also be used to provide aspiration and/or irrigation as desired.

As noted above, in standard angioplasty procedures, a guidewire is first introduced into the patient's vasculature through an incision made in the femoral artery in the groin and advanced through the patient's vasculature until it reaches a site just proximal to a stenosis (narrowing) or occlusion (blockage). The stenosis or occlusion has a length and a width or thickness which at least partially occludes the vessel's lumen. It is to be understood that "occlusion" as used herein includes complete and partial occlusions, stenoses, emboli, thrombi, plaque, and any other substance which at least partially occludes the lumen of the blood vessel.

The guidewire is used to guide the insertion of the exchange catheter, which is positioned such that its distal end is proximal to the occlusion. It is also possible to cross the occlusion with the exchange catheter so that the distal end is distal the occlusion. This is desirable where there may be difficulty crossing the occlusion with the occlusive device, such as a self-expanding filter or braid. It should be noted that, as used herein, "distal" refers to the that end of the apparatus that is inserted into the patient's body, while "proximal" refers to that end which remains outside the patient's body. At this time, the guidewire can be removed through the exchange catheter and a second guidewire or catheter can be inserted and advanced therethrough.

Preferably, the first guidewire is exchanged with a guidewire or catheter having an occlusive device, such as an inflatable balloon, filter or other mechanical occlusive device, mounted on its distal end. The occlusive device should be capable of preventing the migration of particles and debris from the working area, either through total or partial occlusion of the vessel. Note that the occlusion of the vessel need not be complete. Substantial occlusion of the vessel can be sufficient for purposes of the present invention. The catheter is preferably made of metal such as stainless steel or nitinol, plastics, or composites. A guidewire having an occlusive device on its distal end is also suitable for use in the present method. The method of the present invention can be effectively carried out using a number of guidewires or catheters that perform the function of occluding the vessel. The term "catheter" as used herein is therefore intended to include both guidewires and catheters with these desired characteristics.

The occlusive device on the distal end of the occlusion catheter makes the catheter difficult to position within the body. The catheter has a decreased torque response, meaning that the distal tip of the catheter is difficult to manoeuver within the blood vessels using only that portion of the catheter that remains outside the patient's body. By delivering the occlusion catheter through an exchange catheter, insertion is simplified. The lumen of the exchange catheter provides an easily accessible pathway for the occlusion catheter to follow to the site of the occlusion.

Once the occlusion catheter has been properly positioned inside the vessel, the exchange catheter is removed, and a therapy catheter is delivered to the site of the occlusion. The term "therapy catheter" is meant to include any of a number of known devices used to treat an occluded vessel. For example, a catheter carrying an inflatable balloon for use in balloon angioplasty can be delivered to dilate the occlusion. Thermal balloon angioplasty includes the use of heat to "mold" the vessel to the size and shape of the angioplasty balloon. Similarly, an intravascular stent can be delivered via a balloon catheter and deployed at the site of the occlusion to keep the vessel open. Cutting, shaving, scraping or pulverizing devices can be delivered to excise the occlusion in a procedure known as atherectomy. A laser or ultrasound device can also be delivered and used to ablate plaque in the vessel. Various thrombolytic or other types of drugs can be delivered locally in high concentrations to the site of the occlusion. It is also possible to deliver various chemical substances or enzymes via a catheter to the site of the occlusion to dissolve the obstruction. The term "therapy catheter" encompasses these and similar devices.

Once the therapy catheter is in place, the occlusive device at the distal end of the occlusion catheter is actuated to occlude the vessel distal to the existing occlusion to create a working area and to prevent migration of particles and debris downstream. Therapy is performed to remove or reduce the occlusion using any of the methods and apparatus described above. The therapy catheter is removed and the working area is aspirated, if desired, to remove fluid and debris. Aspiration pressure can be provided through the exchange catheter if desired. A source of negative pressure is attached at the proximal end of the exchange catheter, either directly or through a valve and/or extension line, to create reverse flow. The distal end of the exchange catheter is delivered to the working area, and fluid and debris are aspirated through the exchange catheter's main lumen. Alternatively, an aspiration catheter or similar debris removing device is delivered to the working area to remove particles and any other debris. The term "aspiration catheter" includes any device which creates an area of fluid turbulence and uses negative pressure and reverse flow to aspirate fluid and debris, and includes those devices which create a venturi effect within the vessel.

Irrigation fluid may also be provided through the exchange catheter if desired. A source of irrigation fluid, such as saline, is connected to the proximal end of the catheter, and the fluid is delivered through the exchange catheter's main lumen. Irrigation and aspiration can be alternately provided through the catheter if desired. Contrast solution may also be delivered through the exchange catheter should fluoroscopy or local angiography be desired. Following aspiration and/or irrigation or delivery of contrast solution, the occlusive device is deactivated and the catheter and guidewire are removed from the patient.

Occlusion Catheter

Figure 2:
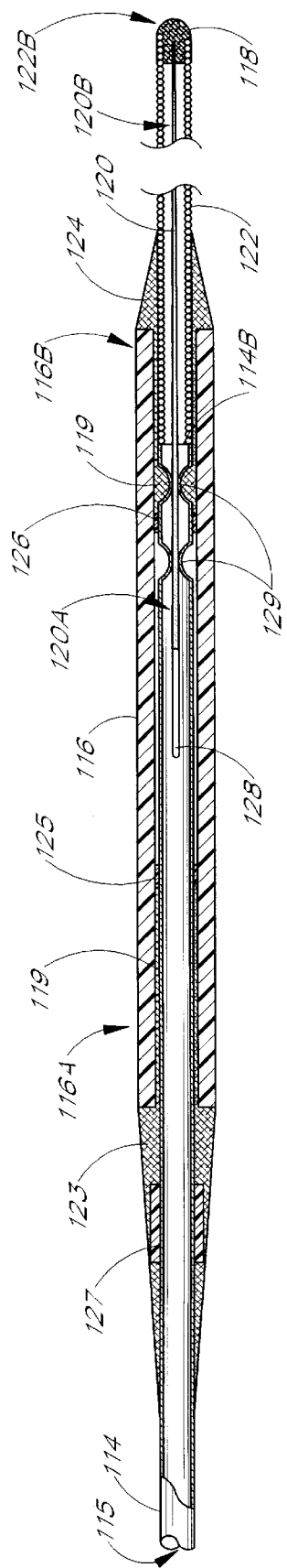
FIG. 2 is schematic cross-sectional view of a distal portion of the occlusion catheter of FIG. 1.

An occlusion catheter suitable for use in the present invention is illustrated in FIGS. 1 and 2. The catheter apparatus 110 is generally comprised of four communicating members including an elongated tubular member 114, an inflatable balloon member 116, a core-wire member 120 and a coil member 122. The catheter apparatus 110 is preferably provided with an outer coating of a lubricous material, such as TEFLON.

The body member 114 of the catheter apparatus 110 is in the form of hypotubing and is provided with proximal and distal ends 114A and 114B as well as an inner lumen 115 extending along the tubular member 114. The balloon member 116 is coaxially mounted on the distal end 114B of the tubular member 114 by suitable adhesives 119 at a proximal end 116A and a distal end 116B of the balloon member 116 as in the manner shown in FIG. 2. Proximal and distal tapered portions 123 and 124 on either side of the balloon 116 preferably include adhesives. Proximal and distal adhesive stops 125 and 126 contact the adhesives 119 to define the working length of the balloon 116. A radiopaque marker 127 is preferably located within the proximal tapered portion 123. A notch 128 in the tubular member 114 permits fluid communication between the lumen 115 and the balloon 116.

A core-wire member 120 of the catheter 110 may be comprised of a flexible wire. The flexible wire 120 is preferably secured to the tubular member 114 within the lumen 115 by a combination of adhesives and crimps 129 (FIG. 2). The proximal end 120A of the flexible wire 120 can have a transverse cross sectional area substantially less than the smallest transverse cross-sectional area of the inner lumen 115 of the tubular member 114. The flexible wire 120 can also taper towards the distal end 120B to smaller diameters to provide greater flexibility to the flexible wire 120. However, the flexible wire 120 may be in the form of a solid rod, ribbon or a helical coil or wire or combinations thereof. As shown in FIG. 2, the distal end 120B of the flexible wire 120 is secured to a rounded plug 118 of solder or braze at the distal end 122B of the coil member 122. The coil member 122 of the catheter 110 may be comprised of a helical coil. The coil member 122 is coaxially disposed about the flexible wire 120, and is secured to the flexible wire 120 by soldering or brazing.

The balloon member 116 is preferably a compliant balloon formed of a suitable elastic material such as a latex or the like. The flexible coil 122 is preferably formed of a wire of platinum or gold based alloys. The flexible core-wire 120 and the tubular member 114 are preferably formed of a superelastic nickel-titanium alloy.

The catheters of the present invention are preferably provided with a coating on the outer surface, or on both the inner and outer surfaces. Suitable coatings include hydrophilic, hydrophobic and antithrombogenic coatings. Examples include heparin, silicone, polyurethane and PVP. These coatings can be applied using methods well known in the art.

Additional details relative to the catheters described above are found in copending U.S. patent applications Ser. Nos. 08/813,023 and 08/812,876, filed Mar. 6, 1997, entitled "Catheter for Emboli Containment" and "Hollow Medical Wires and Methods of Constructing Same", and U.S. Patent Applications entitled "Low Profile Catheter Valve and Inflation Adaptor", Attorney Docket No. PERCUS.006CP1, filed Nov. 20, 1997, "Balloon Catheter and Method of Manufacture", Attorney Docket No. PERCUS.010CP1, filed on the same date as the present application, "Core Wire With Shapeable Tip", Attorney Docket No. PERCUS.053A, filed on the same date as the present application, and "Shaft for Medical Catheters", Attorney Docket No. PERCUS.055A, filed on the same date as the present application, all of which are hereby incorporated by reference in their entirety.

Exchange Catheters

As noted above, the present invention provides for the removal of a standard guidewire and replacement with a guidewire or catheter bearing an occlusive device. The exchange catheters can also be used to provide aspiration and/or fluid delivery as desired.

Various embodiments of the exchange catheter are illustrated in FIGS. 3 through 15. Note that like parts are denoted with like reference numerals throughout the figures and description. The elongate catheter shaft 210 must have sufficient structural integrity, or "stiffness," to permit the catheter 200 to be pushed through the vasculature to distal blood vessel locations without buckling or undesirable bending of the body 210. It is also desirable, however, for the body 210 to be fairly flexible near its distal end, so that the tubular body 210 may be navigated through tortuous blood vessel networks and to prevent injury to the patient during insertion of the catheter 200. Thus, in one preferred embodiment, the tubular body 210 of the exchange catheter 200 is formed from a polymer such as polyethylene, polyimide, polyether etherketone (PEEK) or PEBAX (Atochem, France) made to have variable stiffness along its length, with the proximal portion 202 of the tubular body 210 being less flexible than the distal portion 204 of the body 210. Advantageously, a tubular body 210 of this construction enables a user to more easily insert the tubular body 210 into vascular networks difficult to access using conventional catheters of uniform stiffness. This is because the stiffer proximal portion 202 provides the requisite structural integrity needed to advance the catheter 200 without buckling, while the more flexible distal region 204 is more easily advanced into and through tortuous blood vessel passageways.

In one preferred embodiment, variable stiffness along the length of the catheter shaft 210 is achieved by forming a polymeric tubular body 210 which incorporates a reinforcement along its length. For example, the tubular body 210 may be provided with a reinforcing braid or coil incorporated into its wall structure. The reinforcement can be formed of metal or of various polymers. To achieve variable stiffness, the proximal region of the catheter 202 is provided with a braid or coil having a lower braid or coil density than that present in the braid or coil of the distal region 204. The lower braid density in the proximal region 202, along with the polymer used to form the catheter body, makes it less flexible, or "stiffer", than the distal region of the catheter 204.

The precise density of the braiding or coiling provided to the proximal 202, distal 204 and transition regions can be varied considerably at the time of manufacture, such that catheters 200 having a variety of different flexibility profiles may be created. Moreover, the braid or coil density may be varied within the catheter regions 202, 204 as well, by providing a braid or coil which has a braid or coil density gradient along its length. For example, the most proximal part of the proximal region 202 may be provided with a metallic braid having a braid density of about 50–90 picks per inch, with the braid density increasing at a rate of about 2–10 picks per inch as the raid extends in the distal direction. This reinforced construction of the catheter 200 provides adequate proximal stiffness for axial push, while the distal tip 206 remains softer and more flexible, thereby preventing injury to the patient.

A variety of different materials, known to be ductile and shapeable into fine wires, may be used to form the reinforcement. For example, various polymers, stainless steel, silver or gold plated stainless steel, platinum, nitinol, or a combination thereof are suitable. In one preferred embodiment, the braid is formed of stainless steel, and has a braid density which varies from 50–70 picks per inch at the most proximal part of the proximal region of the catheter 202, to 80–100 picks per inch at the most distal part of the distal region of the catheter 204.

Reinforcing braids or coils may be introduced into the structure of the catheter body 210 through conventional catheter forming techniques. For example, the tubular body 210 may be formed by inserting a 72D PEBAX tube into a variable braid density stainless steel sleeve, and then inserting the sleeved tube into a 72D PEBAX outer tube of the same length, so that the braided sleeve is sandwiched between the two tubes. A shaping mandrel may be inserted within the inner PEBAX tube, and shaping container over the outer PEBAX tube, and the entire apparatus may then be placed in a hot box kept at a temperature slightly greater than the melting temperature of the PEBAX tubes. The PEBAX tubes will melt and fuse together, and once cooled, will form a tubular body 210 incorporating the braid. This same technique can be used to form a tubular body 210 incorporating a coil.

In another embodiment, variable stiffness of the tubular body 210 may be achieved by forming the proximal 202 and distal regions 204 of the tubular body 210 out of polymeric materials having differing degrees of stiffness. For example, the distal 10–35 cm of the catheter body 204 may be formed of a flexible material such as 50% high density polyethylene (HDPE) and 50% low density polyethylene (LDPE). The remainder of the length of the catheter body 210 is formed of stiffer materials such as a combination of 75% HDPE and 25% LDPE. More or less flexible materials may be used as desired to alter the flexibility of the resulting tubular body.

Furthermore, the flexibility of the various regions of a tubular body 210 formed in this manner may be varied further by incorporating a braid or coil having either a uniform braid density or coil pitch, or a varying density or coil, into the tubular body, as described above.

Moreover, any of a variety of different polymeric materials known by those of skill in the art to be suitable for catheter body manufacture may be used to form the exchange catheter body 210. For example, the body 210 may be formed out of polymers such as polyethylene, PEBAX, polyimide, polyether etherketone, and the like. Different materials might also be combined to select for desirable flexibility properties.

Also, although the exchange catheter body 210 has been described in the context of having two regions of differing flexibility, it will be readily appreciated by those of skill in the art that three or more regions of differing flexibility may easily be provided, by adapting the teachings contained herein.

The distal end 204 of the exchange catheter 200 preferably incorporates a radiopaque filler or marker 208. Advantageously, radiopaque material serves as a marker 208 to help the user position the catheter 200 inside the patient's body. Various well-known radiopaque materials may be used at the distal end 204 to form the marker 208, such as platinum or gold. Alternatively, $BaSO_4$ can be incorporated into the polymer resin itself.

Single Lumen Catheter

The hollow exchange catheter 200 is approximately 135–140 cm in length, but of course can be shorter or longer if desired. In the embodiment shown in FIGS. 203 and 4, the catheter body 210 has a single lumen 212 which runs the length of the catheter body, from the proximal end to the distal end. The lumen 212 is illustrated in FIG. 4.

The body 210 of the exchange catheter 200 has an inner diameter of approximately 0.045 inches, and an outer diameter of approximately 0.065 inches, which tapers to an inner diameter of approximately .041 inches and an outer diameter of about 0.054 inches near the distal end 204. At its distal tip 206 (the distal most 2–10 mm of the catheter body), the catheter shaft 210 tapers even further, and ends in an inner diameter of about 0.018–0.032 inches at the most distal 0.5–5 mm of the catheter shaft 206. To allow for unobstructed passage of the occlusive device through the body of the catheter 210, the body 210 should have an inner diameter that is at least 0.005 inches larger than the maximum outer diameter of the occlusive device.

The exchange catheter body 210 has at least one, and preferably two slits 214 in its distal tip. The slit 214 is approximately 3–20 mm in length. As will be explained in more detail below, the slit 214 allows the distal tip of the exchange catheter 206 to expand to allow for the passage of an occlusive device through the distal tip of the catheter 206, while maintaining a very low profile at the distal tip of the catheter 206 to prevent injury to the patient.

The entire length of the catheter shaft 210 may also include a slit that extends from the distal tip 206 to the proximal end 202. This slit allows for the removal of the guidewire through the side of the shaft 210, without the need to remove any adaptors or other fittings from the proximal end of the catheter 202.

The proximal shaft 202 of the exchange catheter 200 may also be provided with a support sheath 216, as illustrated in FIG. 5. The support sheath 216 is located on the proximal end of the catheter 202. The support sheath 216 provides added strength to the catheter body 210. The proximal end of the guide catheter used to assist in the insertion of the exchange catheter 200 may include adaptors and valves. For example, commonly used adaptors and valves include a Touhy-Borst or hemostasis valve, which are positioned at the proximal end of the guide catheter. The hemostasis valve surrounds the outer surface of the exchange catheter 200 when the exchange catheter 200 is positioned within the guide catheter, and tightens down around the catheter 200 to prevent the patient's blood from flowing out around the catheter 200. As the valve is tightened, there is some risk that the exchange catheter 200 may be crushed. Accordingly, a support sheath 218 may be added to the proximal end of the exchange catheter 202 to prevent collapse or crushing of the catheter 200.

In addition, the support sheath 216 allows the exchange catheter 200 to move within the hemostasis valve. The physician may wish to move the distal tip 206 of the exchange catheter 200 within the patient's vessels. If the hemostasis valve is tightened directly onto the exchange catheter 200, the catheter 200 is not free to slide back and forth. If the valve is tightened on the support sheath 216, however, there is a sufficient gap between the support sheath 216 and the body of the exchange catheter 210 to allow for slidable movement of the exchange catheter 200.

The support sheath 216 is preferably about 3–9 cm in length, and more preferably is about 6 cm in length. It is positioned near the proximal end of the exchange catheter 202. The support sheath 216 is preferably formed of polyimide. The sheath 216 surrounds the outer surface of the exchange catheter 200, as shown in FIG. 5, giving that portion of the exchange catheter 200 greater strength and preventing the valve from crushing the lumen 212. This support sheath 216 may, of course, be incorporated into any of the catheters 200 described herein.

Single Lumen Exchange/Aspiration/Irrigation Catheter

A single lumen exchange catheter 200 having aspiration and/or fluid delivery capabilities is illustrated in FIGS. 5 and 6. This catheter 200 is similar to the catheter 200 just described, but in addition to having at least one slit of about 3–20 mm in length at its distal tip 206, this catheter 200 includes at least one larger opening 220 at its distal end 204 for aspiration and/or fluid delivery as well. The opening 220 is approximately 0.5–1.5 mm wide by 1–5 mm long, large enough to allow the occlusive device to pass through. It is located approximately 1–10 mm from the distal tip of the catheter, and can be of any shape, but is preferably rounded or oval.

The proximal end of the catheter 202 is preferably attached to an adaptor, such as the two-armed or "Y" adaptor 222 illustrated in FIG. 5. During use, one of the arms 224 is connected to a source of negative pressure to provide aspiration, or to a source of fluid to provide irrigation or contrast solution. The other port 226 also provides access to and from the exchange catheter's lumen 212 for the occlusion catheter, and also accommodates the guidewire.

Dual Lumen Catheter

Another embodiment of the exchange catheter 200 of the present invention is illustrated in FIGS. 7 and 8. This catheter 200 comprises a first lumen 212 to allow for the insertion of occlusion catheter, and to provide aspiration or fluid delivery, as well as a second, separate guidewire lumen 230. The first or main lumen 212 has an inner diameter of approximately 0.046 to 0.054 inches, while the second lumen 230 is much smaller, with an inner diameter of approximately 0.016 to about 0.022 inches. The position of the two lumens 212, 230 with respect to each other is illustrated in FIG. 8. Preferably, the distal end of the main lumen 228 comprises at least one slit of approximately 3–20 mm in length. As described above, the slit allows the distal end of the lumen 228 to expand to accommodate the passage of an occlusive device, if necessary. The catheter 200 may also include a radiopaque marker 208 on its distal end 204.

At the proximal end of the catheter 202, the guidewire lumen 230 ends just distal to the proximal end of the aspiration lumen 212. This allows for the proximal end of the guidewire to exit the guidewire lumen 230. The aspiration lumen 212 is open at the proximal end of the catheter 202, and is preferably connected with a hub or adaptor 222 to allow a source of negative pressure or of fluid to be connected to the main lumen 212.

The proximal end of the catheter 202 may also include a reinforcement or strain relief portion 205. The adaptor 222 is commonly made of hard molded plastic. The catheter 200 is made of much softer, more flexible material. There is a possibility that the catheter body 210 may kink at the junction between the adaptor 22 and the catheter body 210. To reduce the possibility of kinking, a few centimeters of plastic tubing are preferably placed between the catheter body 210 and the adaptor 222. This strain relief portion 205 therefore helps ease the transition between the catheter shaft 210 and the adaptor.

Figure 9:
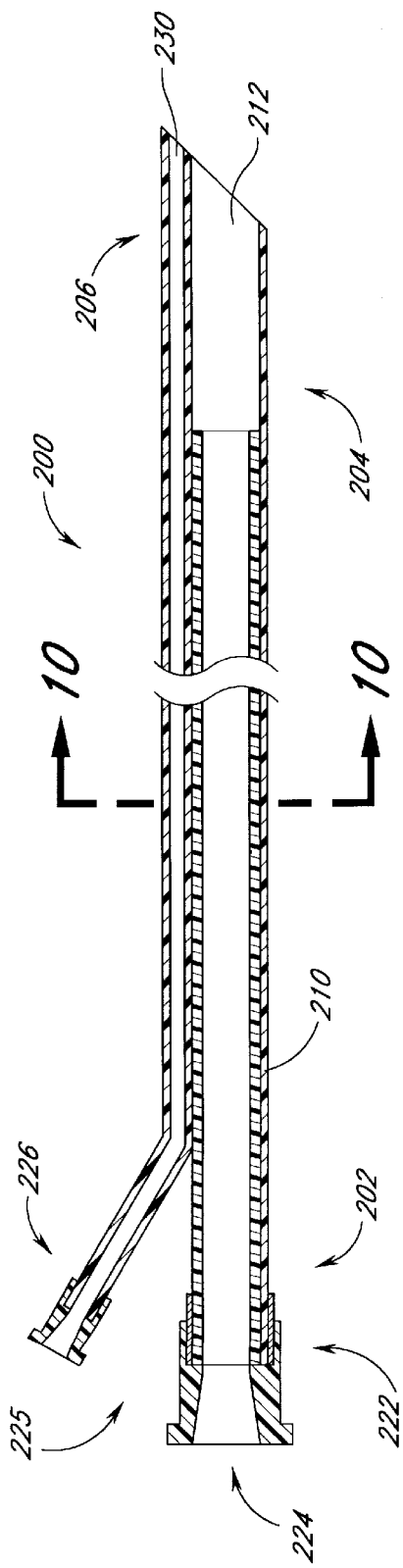
FIG. 9 is a cross-sectional view of another embodiment of a dual lumen exchange catheter.
Figure 10:
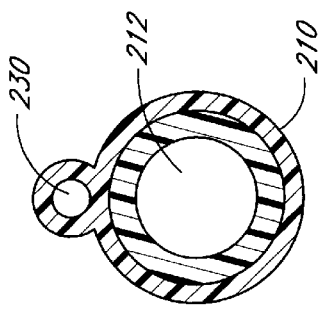
FIG. 10 is a cross-sectional view of the dual lumen exchange catheter taken along line 10—10 of FIG. 9.

One such embodiment of the dual lumen exchange catheter 200 having a Y connector 225 attached at the proximal end 202 is illustrated in FIGS. 9 and 10. One arm of the connector provides a port to which a source of negative pressure 224, such as a syringe, pump, or a source of fluid, such as saline for irrigation or contrast medium, may be attached. This port leads directly into the main lumen of the exchange catheter 212. The other arm 226 of the connector provides the access port for the guidewire. This port 226 connects directly with the guidewire lumen 230 of the exchange catheter 200.

Dual Lumen Catheter with Outer Sleeve

Figure 11:
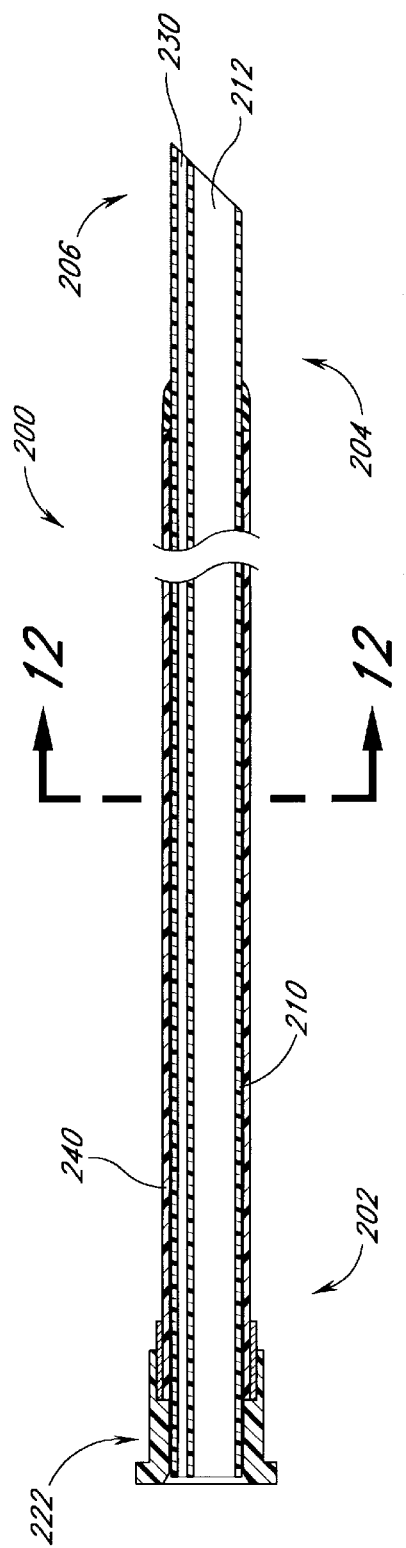
FIG. 11 is a cross-sectional view of another embodiment of a dual lumen exchange catheter having an outer sleeve.
Figure 12:
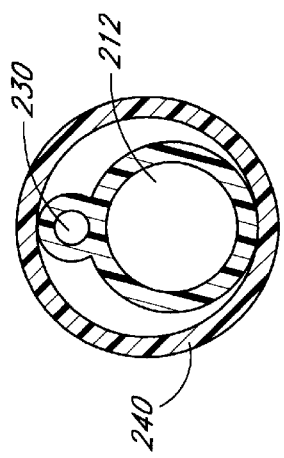
FIG. 12 is a cross-sectional view of the dual lumen exchange catheter of FIG. 11, taken along line 12—12 of FIG. 11, showing the support mandrels.

This embodiment of the dual lumen exchange catheter 200 is shown in FIGS. 11 and 12. This embodiment has an outer sleeve 240 which surrounds the catheter shaft 210, including both the aspiration lumen 212 and the guidewire lumen 230, as illustrated in FIG. 12. The sleeve 240 may be a shrink tube made from PET, PE, polyolefin, TEFLON, or other suitable materials, or it may be polyimide, TEFLON, PEEK or other similar extruded or sized tubing. The sleeve 240 extends from the proximal end of the catheter 202 along the length of the catheter shaft 210, and ends approximately 10–35 cm from the distal tip of the catheter 206.

The catheter may also contain 1 or 2 stainless steel mandrels 241 laid along the length of the catheter shaft 210. The mandrel 241, having a diameter of about 0.010 to 0.016 inches, is used to support the catheter body 210, or where there is a need to stiffen the proximal shaft of the catheter 202. The distal end of the mandrel 241 (the distal most 5–40 cm) is tapered down to a smaller diameter of about 0.0020 to 0.0075 inches to obtain a gradual transition in the stiffness of the catheter body 210. The mandrel is secured in place by the outer sleeve 240.

If a stainless steel mandrel is not incorporated into the catheter 200, it is preferable that the tubing 240 is made from a stiff material such as PET, PEEK, or polyimide in order to lend sufficient support to the catheter body 210.

The outer sleeve 240 and the support mandrel may, of course, be incorporated into any of the catheters 200 described herein.

Combined Single/Double Lumen Catheter

Yet another embodiment of the exchange catheter 200 is illustrated in FIGS. 13–15. This catheter has a single lumen 212 at its proximal end, which becomes a double lumen 230, 212 at the distal end of the catheter shaft 204. The position of the lumens 212, 230 are illustrated in FIGS. 14 and 15. The catheter is made of a dual lumen flexible distal shaft and a single lumen proximal shaft. The single lumen tubing is made from a stiff material such as PET, PEEK, polyimide, or metallic material such as stainless steel or nitinol tubing in order to lend sufficient support to the catheter shaft.

Approximately the most distal 34 cm of the catheter 204 is comprised of two lumens, a main lumen 212 and a smaller guidewire lumen 230. The main lumen 212 has an inner diameter of approximately 0.040 inches, and is adapted to receive the occlusion catheter therethrough, while the guidewire lumen 230 is much smaller, with an inner diameter of approximately 0.018 inches. The guidewire lumen 230 is sized so as to receive the guidewire therethrough. The majority of the length of the catheter body 210 is a single lumen 212, with an inner diameter of approximately 0.050–0.070 inches, which can accommodate both the guidewire and the occlusion catheter. The wall thickness of the catheter is approximately 0.002 to 0.008 inches. Again, the main lumen 212 is preferably provided with at least one slit of about 3–20 mm in length at its distal tip 206 to accommodate passage of the occlusive device. This catheter 200 provides the advantages of a dual lumen catheter, while also providing profile reduction in the proximal region of the catheter body 202.

The proximal end of the catheter 202 preferably is fitted with an adaptor 222, which provides both a port 224 to which a source of negative pressure or fluid is attached, and a guidewire access port.

Exchange Method

Methods of using the exchange catheters will now be described. As explained above, in standard angioplasty procedures, a guidewire is first introduced into the patient's vasculature through an incision made in the femoral artery in the groin and advanced through the patient's vasculature until it reaches a site near to an occlusion. The guidewire is used to guide the insertion of an exchange catheter 200, which is positioned such that its distal end 206 is proximal to the occlusion. The proximal end of the guidewire is inserted into the distal end of the exchange catheter 206, and the exchange catheter 200 is advanced over the wire and into the patient. The guidewire can be inserted either into the main lumen 212 of a single lumen exchange catheter, or into the separate guidewire lumen 230 in a dual lumen exchange catheter. The low profile of the distal tip 206 of the exchange catheter 200 helps to prevent injury to the patient during insertion.

Once the exchange catheter 200 has been advanced to a position near to the occlusion, the guidewire can be withdrawn from the patient through the exchange catheter 200. The guidewire can also remain in place if desired. An occlusion catheter is then inserted into the patient through the lumen of the exchange catheter 212. As the occlusion catheter passes through the low profile of the distal tip 206 of the exchange catheter 200, the slits 214 in the tip allow the catheter 200 to expand to allow the occlusive device to pass through the distal tip of the catheter 206. Alternatively, the occlusive device passes through the aspiration opening 220 at the distal tip of the exchange catheter 206. In either case, the exchange catheter 200 maintains a low profile at its distal tip 206, while also being capable of expanding to allow for the passage of an occlusive device therethrough.

Once the occlusion catheter has been properly positioned inside the vessel, the exchange catheter 200 is removed, and a therapy catheter is delivered to the site of the occlusion. As noted above, the term "therapy catheter" is meant to include any of a number of known devices used to treat an occluded vessel. For example, a catheter carrying an inflatable balloon for use in balloon angioplasty can be delivered to dilate the occlusion. Thermal balloon angioplasty includes the use of heat to "mold" the vessel to the size and shape of the angioplasty balloon. Similarly, an intravascular stent can be delivered via a balloon catheter and deployed at the site of the occlusion to keep the vessel open. Cutting, shaving, scraping or pulverizing devices can be delivered to excise the occlusion in a procedure known as atherectomy. A laser or ultrasound device can also be delivered and used to ablate plaque in the vessel. Various thrombolytic or other types of drugs can be delivered locally in high concentrations to the site of the occlusion. It is also possible to deliver various chemical substances or enzymes via a catheter to the site of the occlusion to dissolve the obstruction.

Once the therapy catheter is in place, the occlusive device at the distal end of the catheter is actuated to occlude the vessel distal to the existing occlusion to create a working area. Therapy is then performed to remove or reduce the size of the occlusion using any of the methods and apparatus described above. The therapy catheter is removed and the working area is aspirated to remove fluid and debris. A separate aspiration catheter can be delivered to the working area, or, alternatively, the exchange catheter 200 can be delivered to provide aspiration. A source of negative pressure is attached at the proximal end of the exchange catheter 202, and fluid and debris are aspirated through the exchange catheter's main lumen 212.

Irrigation fluid and/or contrast media may also be provided through the exchange catheter 200 if desired. A source of irrigation fluid, such a saline, or a source of contrast media, is connected to the proximal end of the catheter 202, and the fluid is delivered through the exchange catheter's main lumen 212. Following aspiration and/or delivery of any desired fluids, the occlusive device is deactivated and the catheter 200 and guidewire are withdrawn from the patient.

While the foregoing detailed description has described several embodiments of the catheters and methods of the present invention, it is to be understood that this description is illustrative only and not limiting of the disclosed invention. It will be appreciated that the specific dimensions of the catheters and guidewires can differ from those described, and the methods described can be used within any biological conduit within the body and remain within the scope of the present invention. Thus, the invention is to be limited only by the claims which follow.

What is claimed is:

1. A catheter exchange method, comprising:

introducing a guidewire having a proximal end and a distal end into the vasculature of a patient until the distal end of the guidewire is near to an occlusion in the vasculature;

providing an exchange catheter comprising an elongate catheter shaft having a proximal end, a distal end, and at least one lumen adapted to allow an occlusive device to pass therethrough, wherein the exchange catheter includes at least one slit in the distal end;

delivering the exchange catheter over the guidewire until the distal end of the exchange catheter is near to the occlusion;

removing the guidewire from the patient;

inserting an occlusion catheter having a proximal end, a distal end and an occlusive device on the distal end thereof into the lumen of the exchange catheter and advancing the occlusion catheter until the occlusive device passes through the distal end of the exchange catheter and is positioned near to the occlusion, wherein passing the occlusion catheter through the distal end of the exchange catheter causes the distal end of the exchange catheter to expand; and removing the exchange catheter from the patient.

2. The method of claim 1, further comprising delivering a therapy catheter to the site of the occlusion and performing therapy to remove or reduce the occlusion.

3. The method of claim 2, further comprising actuating the occlusive device to provide a working area prior to performing therapy.

4. The method of claim 2, further comprising aspirating the working area following performing therapy.

5. The method of claim 4, further comprising removing the therapy catheter following performing therapy, and delivering the distal end of the exchange catheter to the working area and performing the aspirating step using the exchange catheter to deliver aspiration pressure.

6. The method of claim 1, wherein the guidewire is removed prior to inserting the occlusion catheter.

7. The method of claim 1, wherein the guidewire is removed after inserting the occlusion catheter.

8. An exchange method, comprising:

delivering a first guidewire into the vasculature of a patient;

delivering an exchange catheter, the exchange catheter comprising an elongate catheter shaft having a proximal end, a distal end adapted to allow an occlusive device to pass therethrough, and at least one lien extending between the proximal and distal ends, over the first guidewire into the vasculature of the patient;

removing the first guidewire from the patient following delivery of the exchange catheter; and inserting a second guidewire having a proximal end, a distal end, and an occlusive device on the distal end into the at least one lumen of the exchange catheter and advancing the occlusive device through the distal end of the exchange catheter into the vasculature of the patient.

9. The method of claim 8, wherein the first guidewire is removed after insertion and advancement of the second guidewire.

10. The method of claim 8, further comprising removing the exchange catheter.

11. The method of claim 10, further comprising delivering a therapy catheter for performing therapy after removing the exchange catheter.

12. The method of claim 11, further comprising actuating the occlusive device prior to performing therapy.

13. An exchange catheter method, comprising:

delivering a first guidewire having a proximal end and a distal end into the vasculature of the patient until the distal end of the guidewire is near to an occlusion;

delivering an exchange catheter comprising an elongate catheter shaft having a proximal end, a distal end and at least one lumen extending therethrough, over the guidewire until the distal end of the exchange catheter is near to the occlusion;

delivering a second guidewire having a proximal end, a distal end and an occlusive device on the distal end of the second guidewire through a lumen of the exchange catheter without riding over the first guidewire until the occlusive device is positioned near to the occlusion; and removing the first guidewire following delivery of the exchange catheter.

14. The method of claim 13, wherein the exchange catheter has two lumens.

15. The method of claim 14, wherein the exchange catheter is delivered over the guidewire through one of the two lumens.

16. The method of claim 15, wherein the second guidewire is delivered through the other of the two lumens.

17. The method of claim 13, wherein the second guidewire is delivered adjacent the first guidewire.

18. The method of claim 13, wherein removing the first guidewire occurs prior to delivery of the second guidewire.

19. The method of claim 13, further comprising removing the exchange catheter following delivery of the second guidewire.

20. The method of claim 19, further comprising delivering a therapy catheter for performing therapy on the occlusion after removing the exchange catheter.

21. The method of claim 20, further comprising actuating the occlusive device prior to performing therapy.

22. An exchange method for performing therapy in the vasculature of a patient, comprising:

delivering a first guidewire having a proximal end and a distal end into the vasculature of the patient until the distal end of the guidewire is near to an occlusion;

delivering an exchange catheter comprising an elongate catheter shaft having a proximal end, a distal end and at least one lumen extending therethrough, over the guidewire until the distal end of the exchange catheter is near to the occlusion;

delivering a second guidewire having a proximal end, a distal end and an occlusive device on the distal end of the second guidewire through a lumen of the exchange catheter until the occlusive device is positioned near to the occlusion;

removing the first guidewire from the patient following delivery of the exchange catheter and prior to performing therapy; and removing the exchange catheter from the patient following delivery of the second guidewire.

* * * * *

UNITED STATES PATENT AND TRADEMARK OFFICE
Certificate

Patent No. 6,159,195                                                                               Patented: December 12, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Hung V. Ha, San Jose, CA; and Gholam-Reza Zadno-Azizi, Newark, CA.

Signed and Sealed this Tenth Day of June 2003.

<div align="right">
BRIAN L. CASLER<br>
<em>Supervisory Patent Examiner</em><br>
Art Unit 3763
</div>

UNITED STATES PATENT AND TRADEMARK OFFICE
CERTIFICATE OF CORRECTION

PATENT NO. : 6,159,195
DATED : December 12, 2000
INVENTOR(S) : Hung V. Ha and Reza-Gholam Zadno-Azizi It is certified that error appears in the above-identified patent and that said Letters Patent is hereby corrected as shown below:

<u>Column 13,</u>
Line 32, "lien" should read -- lumen --.

Signed and Sealed this

Sixteenth Day of May, 2006

JON W. DUDAS
*Director of the United States Patent and Trademark Office*